United States Patent [19]
Canich et al.

US005227440A

[11] Patent Number: 5,227,440
[45] Date of Patent: * Jul. 13, 1993

[54] MONO-CP HETEROATOM CONTAINING GROUP IVB TRANSITION METAL COMPLEXES WITH MAO: SUPPORTED CATALYSTS FOR OLEFIN POLYMERIZATION

[75] Inventors: Jo Ann M. Canich, Webster; Gary F. Licciardi, Humble, both of Tex.

[73] Assignee: Exxon Chemical Patents Inc., Linden, N.J.

[*] Notice: The portion of the term of this patent subsequent to Jun. 25, 2008 has been disclaimed.

[21] Appl. No.: 751,392

[22] Filed: Aug. 28, 1991

Related U.S. Application Data

[60] Division of Ser. No. 581,869, Sep. 13, 1990, Pat. No. 5,057,475, which is a continuation-in-part of Ser. No. 533,245, Jun. 4, 1990, Pat. No. 5,055,438, which is a continuation-in-part of Ser. No. 406,945, Sep. 13, 1989, abandoned.

[51] Int. Cl.$^5$ ............................................ C08F 4/642
[52] U.S. Cl. ................................. 526/129; 526/127; 526/132; 526/150; 526/160; 526/352; 502/103; 502/117; 502/120

[58] Field of Search ............... 526/129, 127, 132, 150, 526/160

[56] References Cited

U.S. PATENT DOCUMENTS

| 4,935,397 | 6/1990 | Chang | 526/129 X |
| 4,937,301 | 6/1990 | Chang | 526/129 X |
| 5,026,798 | 6/1991 | Canich | 526/127 |

FOREIGN PATENT DOCUMENTS

WO87/03887  7/1987  PCT Int'l Appl. ............... 502/117

OTHER PUBLICATIONS

Okuda, Chem. Ber. 123 (1990) pp. 1649-1651.
Shapiro et al., Organometallics, 1990, 9, pp. 867-869.

*Primary Examiner*—Patrick P. Garvin
*Attorney, Agent, or Firm*—Myron B. Kurtzman; Evan K. Butts

[57] ABSTRACT

The invention is a supported catalyst system including an inert support material, a Group IV B transition metal component and an alumoxane component which may be employed to polymerize olefins to produce a high molecular weight polymer.

12 Claims, No Drawings

MONO-CP HETEROATOM CONTAINING GROUP IVB TRANSITION METAL COMPLEXES WITH MAO: SUPPORTED CATALYSTS FOR OLEFIN POLYMERIZATION

This is a division of application Ser. No. 581,869 filed Sep. 13, 1990, now U.S. Pat. No. 5,057,475 which is a continuation-in-part of Ser. No. 533,245 filed Jun. 4, 1990, now U.S. Pat. No. 5,055,438, which is a continuation-in-part of Ser. No. 406,945 filed Sep. 13, 1989, now abandoned.

FIELD OF THE INVENTION

This invention relates to a supported catalyst system comprising an inert support, a monocyclopentadienyl Group IV B transition metal compound and an alumoxane, and to a process using such supported catalyst system for the production of high molecular weight polyolefins, particularly polyethylene and higher poly-α-olefins, and copolymers of ethylene and/or α-olefins with other unsaturated monomers, including diolefins, acetylenically unsaturated monomers and cyclic olefins. The supported catalyst system is highly active at low ratios of aluminum to the Group IV B transition metal, hence catalyzes the production of a polyolefin product containing low levels of catalyst metal residue.

BACKGROUND OF THE INVENTION

As is well known, various processes and catalysts exist for the homopolymerization or copolymerization of olefins. For many applications it is of primary importance for a polyolefin to have a high weight average molecular weight while having a relatively narrow molecular weight distribution. A high weight average molecular weight, when accompanied by a narrow molecular weight distribution, provides a polyolefin or an ethylene-α-olefin copolymer with high strength properties.

Traditional Ziegler-Natta catalysts system—a transition metal compound cocatalyzed by an aluminum alkyl—are capable of producing polyolefins having a high molecular weight but a broad molecular weight distribution.

More recently a catalyst system has been developed wherein the transition metal compound has two or more cyclopentadienyl ring ligands—such transition metal compound being referred to as a metallocene—which catalyzes the production of olefin monomers to polyolefins. Accordingly, metallocene compounds of a Group IV B metal, particularly, titanocenes and zirconocenes, have been utilized as the transition metal component in such "metallocene" containing catalyst system for the production of polyolefins and ethylene-α-olefin copolymers. When such metallocenes are cocatalyzed with an aluminum alkyl—as is the case with a traditional type Ziegler-Natta catalyst system—the catalytic activity of such metallocene catalyst system is generally too low to be of any commercial interest.

It has since become known that such metallocenes may be cocatalyzed with an alumoxane—rather than an aluminum alkyl—to provide a metallocene catalyst system of high activity for the production of polyolefins.

The zirconium metallocene species, as cocatalyzed or activated with an alumoxane, are commonly more active than their hafnium or titanium analogues for the polymerization of ethylene alone or together with an α-olefin comonomer. When employed in a non-supported form—i.e., as a homogeneous or soluble catalyst system—to obtain a satisfactory rate of productivity even with the most active zirconium species of metallocene typically requires the use of a quantity of alumoxane activator sufficient to provide an aluminum atom to transition metal atom ratio (Al:TM) of at least greater than 1000:1; often greater than 5000:1, and frequently on the order of 10,000:1. Such quantities of alumoxane impart to a polymer produced with such catalyst system an undesirable content of catalyst metal residue, i.e., an undesirable "ash" content (the nonvolatile metal content). In high pressure polymerization procedures using soluble cata;yst systems wherein the reactor pressure exceeds about 500 bar only the zirconium or hafnium species of metallocenes may be used. Titanium species of metallocenes are generally unstable at such high pressures unless deposited upon a catalyst support.

A wide variety of Group IV B transition metal compounds have been named as possible candidates for an alumoxane cocatalyzed catalyst system. Although bis(cyclopentadienyl) Group IV B transition metal compounds have been the most preferred and heavily investigated for use in alumoxane activated catalyst systems for polyolefin production, suggestions have appeared that mono and tris(cyclopentadienyl) transition metal compounds may also be useful. See, for example U.S. Pat. Nos. 4,522,982; 4,530,914 and 4,701,431. Such mono(cyclopentadienyl) transition metal compounds as have heretofore been suggested as candidates for an alumoxane activated catalyst system are mono(cyclopentadienyl) transition metal trihalides and trialkyls.

More recently, International Publication No. WO 87/03887 describes the use of a composition comprising a transition metal coordinated to at least one cyclopentadienyl and at least one heteroatom ligand as a transition metal component for use in an alumoxane activated catalyst system for α-olefin polymerization. The composition is broadly defined as a transition metal, preferably of Group IV B of the Periodic Table, which is coordinated with at least one cyclopentadienyl ligand and one to three heteroatom ligands, the balance of the transition metal coordination requirement being satisfied with cyclopentadienyl or hydrocarbyl ligands. Catalyst systems described by this reference are illustrated solely with reference to transition metal compounds which are metallocenes, i.e., bis(cyclopentadienyl) Group IV B transition metal compounds.

Even more recently, at the Third Chemical Congress of North American held in Toronto, Canada in June 1988, John Bercaw reported upon efforts to use a compound of a Group III B transition metal coordinated to a single cyclopentadienyl heteroatom bridged ligand as a catalyst system for the polymerization of olefins. Although some catalytic activity was observed under the conditions employed, the degree of activity and the properties observed in the resulting polymer product were discouraging of a belief that such monocyclopentadienyl transition metal compound could be usefully employed for commercial polymerization processes.

The new metallocene catalyst of the copending application is, however, a homogeneous catalyst and generally cannot be practically used for gas phase polymerization. The use of a supported catalyst offers the possibility of gas phase compatibility. Control of the particle size distribution of the polymeric product in the various polymerization processes eliminates or reduces the extent of reactor fouling.

Supported catalysts for olefin polymerization are well known in the art. These catalysts offer, among others, the advantages of being usable in gas or slurry phase reactors allowing the control of polymer particle size and thereby the control of product bulk density. Gas phase reactors also eliminate the need for a solvent and the equipment for solvent handling and separation. However, the known Ziegler-Natta olefin polymerization supported catalysts also present disadvantages which include broad MWD and composition distribution (CD), inefficient incorporation of comonomers, poor sequence distribution and, in the case of lower activity catalysts, the need for a product deashing step.

Supported metallocene-alumoxane catalysts systems for olefin polymerization are described in U.S. Pat. No. 4,701,432 of Welborn. These supported metallocene-alumoxane catalysts are obtained by reacting a metallocene and an alumoxane in the presence of the solid support material. The supported catalyst may then be employed either as the sole catalyst component or may be employed in combination with an organometallic cocatalyst. The supported metallocene-alumoxane catalyst, however, still produced polymers of generally lower molecular weight and comonomer incorporation than desired for certain applications.

A need still exists for discovering catalyst systems that permit the production of higher molecular weight polyolefins and desirably with a narrow molecular weight distribution. It is also desirable that a catalyst be discovered which, within reasonable ranges of ethylene to α-olefin monomer ratios, will catalyze the incorporation of higher contents of α-olefin comonomers in the production of ethylene-α-olefins copolymers. It is highly desirable that such a catalyst system be available and active in a supported form for process applications which require a supported catalyst, such as gas phase polymerization processes and certain slurry polymerization processes, and for purposes of reducing metal residue left in the final product.

SUMMARY OF THE INVENTION

The supported catalyst system of this invention comprises an inert support, a transition metal component from the Group IV B of the Periodic Table of the Elements, CRC Handbook of Chemistry and Physics, 68th ed. 1987-1988) and an alumoxane component which may be employed in solution, slurry, gas-phase, or bulk phase polymerization procedures, or combinations thereof, to produce a polyolefin of high average molecular weight and relatively narrow molecular weight distribution.

The "Group IV B transition metal component" of the catalyst system is represented by the formula:

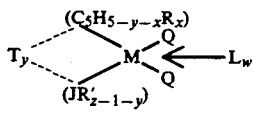

wherein:

M is Zr, Hf or Ti in its highest formal oxidation state (+4, $d^0$ complex);

$(C_5H_{5-y-x}R_x)$ is a cyclopentadienyl ring which is substituted with from zero to five substituent groups R, "x" is 0, 1, 2, 3, 4 or 5 denoting the degree of substitution, and each substituent group R is, independently, a radical selected from a group consisting of $C_1-C_{20}$ hydrocarbyl radicals, substituted $C_1-C_{20}$ hydrocarbyl radicals wherein one or more hydrogen atoms is replaced by a halogen radical, an amido radical, a phosphido radical, an alkoxy radical, alkylborido radicals, or any other radical containing a Lewis acidic or basic functionality, $C_1-C_{20}$ hydrocarbyl-substituted metalloid radicals wherein the metalloid is selected from the Group IV A of the Periodic Table of Elements; and halogen radicals, amido radicals, phosphido radicals, alkoxy radicals, alkylborido radicals or any other radical containing a Lewis acidic or basic functionality, or $(C_5H_{5-y-x}R_x)$ is a cyclopentadienyl ring in which at least two adjacent R-groups are joined forming a $C_4-C_{20}$ ring to give a saturated or unsaturated polycyclic cyclopentadienyl ligand such as indenyl, tetrahydroindenyl, fluorenyl or octahydrofluorenyl;

$(JR'_{z-1-y})$ is a heteroatom ligand in which J is an element with a coordination number of three from Group V A or an element with a coordination number of two from Group VI A of the Periodic Table of Elements, preferably nitrogen, phosphorus, oxygen or sulfur, and each R' is, independently a radical selected from a group consisting of $C_1-C_{20}$ hydrocarbyl radicals, substituted $C_1-C_{20}$ hydrocarbyl radicals wherein one or more hydrogen atoms are replaced by a halogen radical, an amido radical, a phosphido radical, an alkoxy radical, or any other radical containing a Lewis acidic or basic functionality, and "z" is the coordination number of the element J;

each Q may be independently any univalent anionic ligand such as a halide, hydride, or substituted or unsubstituted $C_1-C_{20}$ hydrocarbyl, alkoxide, aryloxide, amide, arylamide, phosphide or arylphosphide, provided that where any Q is a hydrocarbyl such Q is different from $(C_5H_{5-y-x}R_x)$, or both Q together may be an alkylidene or a cyclometallated hydrocarbyl or any other divalent anionic chelating ligand;

"y" is 0 or 1 when w is greater than 0; y is 1 when w is 0; when "y" is 1, T is a covalent bridging group containing a Group IV A or V A element such as, but not limited to, a dialkyl, alkylaryl or diaryl silicon or germanium radical, alkyl or aryl phosphine or amine radical, or a hydrocarbyl radical such as methylene, ethylene and the like;

L is a neutral Lewis base such as diethylether, tetraethylammonium chloride, tetrahydrofuran, dimethylaniline, aniline, trimethylphosphine, n-butylamine, and the like; and "w" is a number from 0 to 3. L can also be a second transition metal compound of the same type such that the two metal centers M and M' are bridged by Q and Q', wherein M' has the same meaning as M and Q' has the same meaning as Q. Such dimeric compounds are represented by the formula:

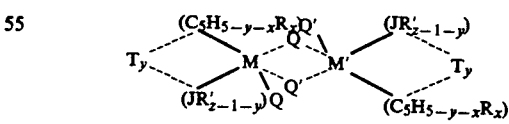

The alumoxane component of the catalyst may be represented by the formulas: $(R^3-Al-O)_m$; $R^4(R^5-Al-O)_mAlR^6$ or mixtures thereof, wherein $R^3-R^6$ are, independently, a $C_1-C_5$ alkyl group or halide and "m" is an integer ranging from 1 to about 50 and preferably is from about 13 to about 25.

The inert support component may be any finely divided solid porous support, including, but not limited to inorganic oxides such as talc, silica, alumina, silica-alumina, or resinous support materials such as polyolefins or mixtures thereof.

Supported catalyst systems of the invention may be prepared by several methods. The "Group IV B transition metal component" and the alumoxane component can be mixed together before the addition of the support material, or the mixture can be added to the support material. The mixture may be prepared in common solution in a normally liquid alkane or aromatic solvent, which solvent is preferably suitable for use as a polymerization diluent for the slurry or bulk phase polymerization of an olefin monomer. Alternatively, the alumoxane can be placed on the support material followed by the addition of the transition metal component or conversely, the transition metal may be applied to the support material followed by the addition of the alumoxane. The alumoxane can be used as commercially supplied, or may be generated in situ on the solid support, for example, by the addition of a trialkylaluminium to a wet support, for example by the addition of trimethylaluminum to wet silica. The supported catalyst may be prepolymerized. In addition, third components can be added in any stage of the preparation of the supported catalyst. Third components can be defined as compounds containing Lewis acidic or basic functionalities exemplified but not limited to compounds such as N,N-dimethylanaline, tetraethoxysilane, phenyltriethoxysilane, bis-tert-butylhydroxy toluene (BHT) and the like.

Those species of the Group IV B transition metal component wherein the metal is titanium have been found to impart beneficial properties to a catalyst system which are unexpected in view of what is known about the properties of bis(cyclopentadienyl) titanium compounds which are cocatalyzed by alumoxanes. Whereas titanocenes in their soluble form are generally unstable in the presence of aluminum alkyls, the monocyclopentadienyl titanium metal components of this invention, particularly those wherein the heteroatom is nitrogen, generally exhibit greater stability in the presence of aluminum alkyls, higher catalyst activity rates and higher α-olefin comonomer incorporation.

Further, the titanium species of the Group IV B transition metal component catalyst of this invention generally produce polymers of greater molecular weight and of higher α-olefin comonomer content than catalyst systems prepared with the zirconium species of the Group IV B transition metal component.

A typical polymerization process of the invention such as for the polymerization or copolymerization of ethylene comprises the steps of contacting ethylene or $C_3$-$C_{20}$ α-olefins alone, or with other unsaturated monomers including $C_3$-$C_{20}$ α-olefins, $C_5$-$C_{20}$ diolefins, and/or acetylenically unsaturated monomers either alone or in combination with other olefins and/or other unsaturated monomers, with a supported catalyst comprising, an inert support material, the Group IV B transition metal component illustrated above; and a methylalumoxane in an amount to provide a molar aluminum to transition metal ratio of from about 1:1 to about 20,000:1 or more; and reacting such monomer in the presence of such supported catalyst system at a temperature of from about $-100°$ C. to about $300°$ C. for a time of from about 1 second to about 10 hours to produce a polyolefin having a weight average molecular weight of from about 1,000 or less to about 5,000,000 or more and a molecular weight distribution of from about 1.5 to about 15.0.

DESCRIPTION OF THE PREFERRED EMBODIMENT

Catalyst Component

The Group IV B transition metal component of the catalyst system is represented by the general formula:

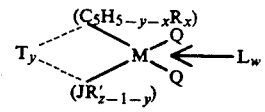

wherein

M is Zr, Hf or Ti in its highest formal oxidation state ($+4$, $d^0$ complex);

$(C_5H_{5-y-x}R_x)$ is a cyclopentadienyl ring which is substituted with from zero to five substituent groups R, "x" is 0, 1, 2, 3, 4 or 5 denoting the degree of substitution, and each substituent group R is, independently, a radical selected from a group consisting of $C_1$-$C_{20}$ hydrocarbyl radicals, substituted $C_1$-$C_{20}$ hydrocarbyl radicals wherein one or more hydrogen atoms is replaced by a halogen radical, an amido radical, a phosphido radical, an alkoxy radical, an alkylborido radical, or other radical containing a Lewis acidic or basic functionality, $C_1$-$C_{20}$ hydrocarbyl-substituted metalloid radicals wherein the metalloid is selected from the Group IV A of the Periodic Table of Elements; and halogen radicals, amido radicals, phosphido radicals, alkoxy radicals, alkylborido radicals, or any other radical containing a Lewis acidic or basic functionality, or $(C_5H_{5-y-x}R_x)$ is a cyclopentadienyl ring in which two adjacent R-groups are joined forming $C_4$-$C_{20}$ ring to give a saturated or unsaturated polycyclic cyclopentadienyl ligand such as indenyl, tetrahydroindenyl, fluorenyl or octahydrofluorenyl;

$(JR'_{z-1-y})$ is a heteroatom ligand in which J is an element with a coordination number of three from Group V A or an element with a coordination number of two from Group VI A of the Periodic Table of Elements, preferably nitrogen, phosphorus, oxygen or sulfur with nitrogen being preferred, and each R' is, independently a radical selected from a group consisting of $C_1$-$C_{20}$ hydrocarbyl radicals, substituted $C_1$-$C_{20}$ hydrocarbyl radicals wherein one or more hydrogen atoms is replaced by a halogen radical, an amido radical, a phosphido radical, an alkoxy radical, an alkylborido radical or other radical containing a Lewis acidic or basic functionality, and "z" is the coordination number of the element J;

each Q is, independently, any univalent anionic ligand such as a halide, hydride, or substituted or unsubstituted $C_1$-$C_{20}$ hydrocarbyl, alkoxide, aryloxide, amide, arylamide, phosphide or arylphosphide, provided that where any Q is a hydrocarbyl such Q is different from $(C_5H_{5-y-x}R_x)$, or both Q together may be an alkylidene or a cyclometallated hydrocarbyl or any other divalent anionic chelating ligand;

"y" is 0 or 1 when w is greater than 0, and y is 1 when w equals 0; when "y" is 1, T is a covalent bridging group containing a Group IV A or V A element such as, but not limited to, a dialkyl, alkylaryl or diaryl silicon or germanium radical, alkyl or aryl phosphine or amine radical, or a hydrocarbyl radical such as methylene, ethylene and the like; and L is a neutral Lewis base such as diethylether, tetrahydrofuran, dimethylaniline, aniline, trimethylphosphine, n-butylamine, and the like; and "w" is a number from 0 to 3; L can also be a second transition metal compound of the same type such that the two metal centers M and M' are bridged by Q and Q', wherein M' has the same meaning as M and Q' has the same meaning as Q. Such compounds are represented by the formula:

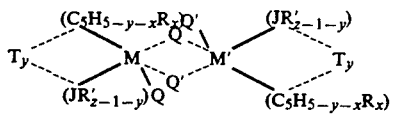

Examples of the T group which are suitable as a constituent group of the Group IV B transition metal component of the catalyst system are identified in column 1 of Table 1 under the heading "T".

Exemplary hydrocarbyl radicals for Q are methyl, ethyl, propyl, butyl, amyl, isoamyl, hexyl, isobutyl, heptyl, octyl, nonyl, decyl, cetyl, 2-ethylhexyl, phenyl and the like, with methyl being preferred. Exemplary halogen atoms for Q include chlorine, bromine, fluorine and iodine, with chlorine being preferred. Exemplary alkoxides and aryloxides for Q are methoxide, phenoxide and substituted phenoxides such as 4-methylphenoxide. Exemplary amides of Q are dimethylamide, diethylamide, methylethylamide, di-t-butylamide, diisoproylamide and the like. Exemplary aryl amides are diphenylamide and any other substituted phenyl amides. Exemplary phosphides of Q are diphenylphosphide, dicyclohexylphosphide, diethylphosphide, dimethylphosphide and the like. Exemplary alkyldiene radicals for both Q together are methylidene, ethylidene and propylidene. Examples of the Q group which are suitable as a constituent group or element of the Group IV B transition metal component of the catalyst system are identified in column 4 of Table 1 under the heading "Q".

Suitable hydrocarbyl and substituted hydrocarbyl radicals, which may be substituted as an R group for at least one hydrogen atom in the cyclopentadienyl ring, will contain from 1 to about 20 carbon atoms and include straight and branched alkyl radicals, cyclic hydrocarbon radicals, alkyl-substituted cyclic hydrocarbon radicals, aromatic radicals and alkyl-substituted aromatic radicals, amido-substituted hydrocarbyl radicals, phosphido-substituted hydrocarbyl radicals, and alkoxy-substituted hydrocarbyl radicals and cyclopentadienyl rings containing one or more fused saturated or unsaturated rings. Suitable organometallic radicals, which may be substituted as an R group for at least one hydrogen atom in the cyclopentadienyl ring, include trimethylsilyl, triethylsilyl, ethyldimethylsilyl, methyldiethylsilyl, triphenylgermyl, trimethylgermyl and the like. Other suitable radicals that may be substituted for one or more hydrogen atoms in the cyclopentadienyl ring include halogen radicals, amido radicals, phosphido radicals, alkoxy radicals, alkylboride radicals, and the like. Examples of cyclopentadienyl ring groups $(C_5H_{5-y-x}R_x)$ which are suitable as a constituent group of the Group IV B transition metal component of the catalyst system are identified in Column 2 of Table 1 under the heading $(C_5H_{5-y-x}R_x)$.

Suitable R' radicals of the heteroatom J ligand are independently a hydrocarbyl radical selected from a group consisting of 1 to about 20 carbon atoms and include straight and branched alkyl radicals, cyclic hydrocarbon radicals, alkyl-substituted cyclic hydrocarbon radicals, aromatic radicals and the like; substituted $C_1$–$C_{20}$ hydrocarbyl radicals wherein one or more hydrogen atom is replaced by a halogen radical, an amido radical, a phosphido radical, an alkoxy radical, and alkylborido radical, or other radical containing a Lewis acidic or basic functionality, and the like. Examples of heteroatom ligand groups $(JR'_{z-1-y})$ which are suitable as a constituent group of the Group IV B transition metal component of the catalyst system are identified in column 3 of Table 1 under the heading $(JR'_{z-1-y})$.

Table 1 depicts representative constituent moieties for the "Group IV B transition metal component", the list is for illustrative purposes only and should not be construed to be limiting in any way. A number of final components may be formed by permuting all possible combinations of the constituent moieties with each other. Illustrative compounds are: dimethylsilyltetramethylcyclopentadienyl-tert-butylamido zirconium dichloride, methylphenylsilyltetramethylcyclopentadienyl-tert-butylamido titanium dichloride, and dimethylsilyltetramethylcyclopentadienylcyclododecylamido titanium dichloride, and the like.

For illustrative purposes, the above compounds and those permuted from Table 1 do not include the neutral Lewis base ligand (L). The conditions under which complexes containing neutral Lewis base ligands such as ether or those which form dimeric compounds is determined by the steric bulk of the ligands about the metal center. For example, the t-butyl group in $Me_2Si(Me_4C_5)$ (N-t-Bu)$ZrCl_2$ has greater steric requirements than the phenyl group in $Me_2Si(Me_4C_5)$ (NPh)$ZrCl_2 \cdot Et_2O$ thereby not permitting ether coordination in the former compound. Similarly, due to the decreased steric bulk of the trimethylsilylcyclopentadienyl group in $[Me_2Si(Me_3SiC_5H_3)$ (N-t-Bu)$ZrCl_2]_2$ versus that of the tetramethylcyclopentadienyl group in $Me_2Si(Me_4C_5)$ (N-t-Bu)$ZrCl_2$, the former compound is dimeric and the latter is not.

TABLE 1

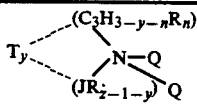

| T (when y = 1) | $(C_3H_{3-y-a}R_a)$ | $(JR'_{a-l-y})$ | Q | R |
|---|---|---|---|---|
| dimethylsilyl | cyclopentadienyl | t-butylamide | hydride | zirbonium. |
| diethylsilyl | methylcyclopentadienyl | phenylamido | chloro | hafnium |
| di-n-propylsilyl | 1,2-dimethylcyclopentadienyl | p-n-butylphenylamido | methyl | titanium |
| diisopropylsilyl | 1,3-dimethylcyclopentadienyl | cyclohexylamido | ethyl | |
| di-n-butylsilyl | indenyl | perflurophenylamido | phenyl | |
| di-t-butylsilyl | 1,2-diethylcyclopentadienyl | n-butylamido | fluoro | |
| di-n-hexylsilyl | tetramethylcyclopentadienyl | methylamido | bromo | |
| methylphenylsilyl | ethylcyclopentadienyl | ethylamido | iodo | |
| ethylmethylsilyl | n-butylcyclopentadienyl | n-propylamido | n-propyl | |

TABLE 1-continued $$T_y \underset{(JR'_{z-1-y})}{\overset{(C_3H_{3-y-n}R_n)}{\diagdown}} N = Q$$

| T (when y = 1) | (C₃H₃₋ᵧ₋ₐRₐ) | (JR'ₐ₋₁₋ᵧ) | Q | R |
|---|---|---|---|---|
| diphenylsilyl | cyclohexylmethylcyclopentadienyl | isopropylamido | isopropyl | |
| di(p-t-butylphenethylsilyl) | n-octylcyclopentadienyl | benzylamido | n-butyl | |
| n-hexylmethylsilyl | β-phenylpropylcyclopentadienyl | t-butylphosphido | amyl | |
| cyclopentamethylenesilyl | tetrahydroindenyl | ethylphosphido | isoamyl | |
| cyclotetramethylenesilyl | propylcyclopentadienyl | phenylphosphido | hexyl | |
| cyclotrimethylenesilyl | t-butylcyclopentadienyl | cyclohexylphosphido | isobutyl | |
| dimethylgermanyl | bensylcyclopentadienyl | oxo (when y = 1) | heptyl | |
| diethylgermanyl | diphenylmethylcyclopentadienyl | sulfido (when y = 1) | octyl | |
| phenylamido | trimethylgermylcyclopentadienyl | methoxide (when y = 0) | nonyl | |
| t-butylamido | trimethylstannylcyclopentadienyl | ethoxide (when y = 0) | decyl | |
| methylamido | triethylplumbylcyclopentadienyl | methylthic (when y = 0) | cetyl | |
| t-butylphosphido | trifluromethylcyclopentadienyl | ethylthic (when y = 0) | methoxy | |
| ethylphosphido | trimethylsilylcyclopentadienyl | | ethoxy | |
| phenylphosphido | pentamethylcycloopentadienyl (when y = 0) | | propoxy | |
| methylene | fluorenyl | | butoxy | |
| dimethylmethylene | octahydrofluoroxyl | | phenoxy | |
| diethylmethylene | N,N-dimethylamidocyclopentadienyl | | dimethylamide | |
| ethylene | dimethylphosphidocyclopentadienyl | | diethylamide | |
| dimethylethylene | methoxycyclopentadienyl | | methylethylamide | |
| diethylethylene | dimethylboridocyclopentadienyl | | di-t-butylamide | |
| dipropylethylene | (N,N-dimethylamidomethyl)- | | diphenylamide | |
| propylene | cyclopentadienyl | | diphenylphosphide | |
| dimethylpropylene | | | dicyclophoxyl- | |
| diethylpropylene | | | phosphide | |
| 1,1-dimethyl-3,3- | | | dimethylphosphide | |
| dimethylpropylene | | | methylidene (both Q) | |
| tetramethyldisiloxane | | | ethylidene (both Q) | |
| 1,1,4,4-tetramethyldisilyl- | | | propylidene (both Q) | |
| ethylene | | | ethyleneglycoldianion (both Q) | |

Generally the bridged species of the Group IV B transition metal compound ("y"=1) are preferred. These compounds can be prepared by reacting a cyclopentadienyl lithium compound with a dihalo compound whereupon a lithium halide salt is liberated and a monohalo substituent becomes covalently bound to the cyclopentadienyl compound. The so substituted cyclopentadienyl reaction product is next reacted with a lithium salt of a phosphide, oxide, sulfide or amide (for the sake of illustrative purposes, a lithium amide) whereupon the halo element of the monohalo substituent group of the reaction product reacts to liberate a lithium halide salt and the amine moiety of the lithium amide salt becomes covalently bound to the substituent of the cyclopentadienyl reaction product. The resulting amine derivative of the cyclopentadienyl product is then reacted with an alkyl lithium reagent whereupon the labile hydrogen atoms, at the carbon atom of the cyclopentadienyl compound and at the nitrogen atom of the amine moiety covalently bound to the substituent group, react with the alkyl of the lithium alkyl reagent to liberate the alkane and produce a dilithium salt of the cyclopentadienyl compound. Thereafter the bridged species of the Group IV B transition metal compound is produced by reacting the dilithium salt cyclopentadienyl compound with a Group IV B transition metal preferably a Group IV B transition metal halide.

Unbridged species of the Group IV B transition metal compound can be prepared from the reaction of a cyclopentadienyl lithium compound and a lithium salt of an amine with a Group IV B transition metal halide.

Suitable, but not limiting, Group IV B transition metal compounds which may be utilized in the catalyst system of this invention include those bridged species ("y"=1) wherein the T group bridge is a dialkyl, diaryl or alkylaryl silane, or methylene or ethylene. Exemplary of the more preferred species of bridged Group IV B transition metal compounds are dimethylsilyl, methylphenylsilyl, diethylsilyl, ethylphenylsilyl, diphenylsilyl, ethylene or methylene bridged compounds. Most preferred of the bridged species are dimethylsilyl, diethylsilyl and methylphenylsilyl bridged compounds.

Suitable Group IV B transition metal compounds which are illustrative of the unbridged ("y"=0) species which may be utilized in the catalyst systems of this invention are exemplified by pentamethylcyclopentadienyldi-t-butylphosphinodimethyl hafnium; pentamethylcyclopentadienyldi-t-butylphosphinomethylethyl hafnium; cyclopentadienyl-2-methylbutoxide dimethyl titanium.

To illustrate members of the Group IV B transition metal component, select any combination of the species in Table 1. An example of a bridged species would be dimethylsilylcyclopentadienyl-t-butylamidodichloro zirconium; an example of an unbridged species would be cyclopentadienyldi-t-butylamidodichloro zirconium.

Generally, wherein it is desired to produce an α-olefin copolymer which incorporates a high content of α-olefin, the species of Group IV B transition metal compound preferred is one of titanium. The most preferred species of titanium metal compounds are represented by the formula:

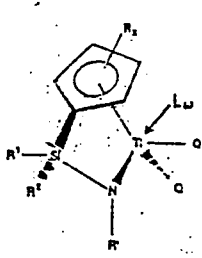

wherein Q, L, R', R, "x" and "w" are as previously defined and $R^1$ and $R^2$ are each independently a $C_1$ to $C_{20}$ hydrocarbyl radicals, substituted $C_1$ to $C_{20}$ hydrocarbyl radicals wherein one or more hydrogen atom is replaced by a halogen atom; $R^1$ and $R^2$ may also be joined forming a $C_3$ to $C_{20}$ ring which incorporates the silicon bridge.

The alumoxane component of the catalyst system is an oligomeric compound which may be represented by the general formula $(R^3-Al-O)_m$ which is a cyclic compound, or may be $R^4(R^5-Al-O-)_m-AlR^6{}_2$ which is a linear compound. An alumoxane is generally a mixture of both the linear and cyclic compounds. In the general alumoxane formula $R^3$, $R^4$, $R^5$ and $R^6$ are, independently a $C_1$-$C_5$ alkyl radical, for example, methyl, ethyl, propyl, butyl or pentyl and "m" is an integer from 1 to about 50. Most preferably, $R^3$, $R^4$, $R^5$ and $R^6$ are each methyl and "m" is at least 4. When an alkyl aluminum halide is employed in the preparation of the alumoxane, one or more $R^{3-6}$ groups may be halide.

As is now well known, alumoxanes can be prepared by various procedures. For example, a trialkyl aluminum may be reacted with water, in the form of a moist inert organic solvent; or the trialkyl aluminum may be contacted with a hydrated salt, such as hydrated copper sulfate suspended in an inert organic solvent, to yield an alumoxane. In another method, non-dehydrated or wet gels, such as wet silica gels may be reacted with trialkyl aluminums. Generally, however prepared, the reaction of a trialkyl aluminum with a limited amount of water yields a mixture of both linear and cyclic species of alumoxane.

Suitable alumoxanes which may be utilized in the supported catalyst systems of this invention are those prepared by the hydrolysis of a trialkylaluminum; such as trimethylaluminum, triethyaluminum, tripropylaluminum; triisobutylaluminum, dimethylaluminumchloride, diisobutylaluminumchloride, diethylaluminumchloride, and the like. The most preferred alumoxane for use is methylalumoxane (MAO). Methylalumoxanes having an average degree of oligomerization of from about 4 to about 25 ("m"=4 to 25), with a range of 13 to 25, are the most preferred.

Inert Support

The normally hydrocarbon soluble transition metal component and alumoxane are prepared as a supported catalyst by deposition on a support material. The support material for preparing the supported catalyst may be any resinous support material such as a polyolefin or any finely divided inorganic solid porous support, such as talc, silica, alumina, silica-alumina, or mixtures thereof. Other inorganic oxides that may be employed either alone or in combination with silica or silica-alumina are magnesia, titania, zirconia, and the like. The inorganic oxides may be dehydrated, as is well known in the art, to remove water. If desired, the residual surface hydroxyl groups in the inorganic solid porous support may be removed by additional heating or by reaction with chemical dehydrating agents such as lithium alkyl, silylchlorides, aluminum aklyls, or preferably with alumoxane. Preferred catalyst supports include dehydrated inorganic oxide treated with an alumoxane, more preferably with methylalumoxane. A suitable support material of this type is a dehydrated silica gel treated with methylalumoxane. When such a alumoxane-treated support is utilized in the production of the supported catalyst, it may not be necessary to include additional alumoxane in the catalyst composition. Also preferred as a catalyst support is a wet gel, more preferably a wet silica gel, containing up to approximately 20% by weight absorbed water. Wet gels may be directly mixed with trialkyl aluminums to form the alumoxane component of the catalyst system.

The specific particle size, surface area and pore volume of the inorganic support material determine the amount of inorganic support material that is desirable to employ in preparing the catalyst compositions, as well as affecting the properties of polymers formed with the aid of the catalyst compositions. These properties must frequently be taken into consideration in choosing an inorganic support material for use in a particular aspect of the invention. A suitable inorganic support such as silica would have a particle diameter in the range of 0.1–600 microns, preferably 0.3–100 microns; a surface area of 50–1000 $m^2/g$, preferably 100–500 $m^2/g$; and a pore volume of 0.5–3.5 $cm^3/g$. To insure its use in dehydrated form the support material may be heat treated at 100°–1000° C. for a period of 1–100 hours, preferably 3–24 hours. The treatment may be carried out in a vacuum or while purging with a dry inert gas such as nitrogen. As an alternative, the support material may be chemically dehydrated. The chemical dehydration is accomplished by slurrying the support in an inert low boiling solvent such as, for example, heptane, in the presence of the dehydrating agent such as for example, triethylaluminum in a moisture and oxygen-free atmosphere.

Catalyst Systems-Method and Use

The Supported Catalyst—Preparation Method 1

The supported catalyst of this invention can be prepared by combining in any order the Group IV B transition metal component, an alumoxane component, and the support in one or more suitable solvents or diluents. Suitable solvents and/or diluents include, but are not necessarily limited to, straight and branched-chain hydrocarbons such as isobutane, butane, pentane, hexane, heptane, octane and the like; cyclic and alicyclic hydrocarbons such as cyclohexane, cycloheptane, methylcyclohexane, methylcyclopentane and the like; and aromatic and alkyl-substituted aromatic compounds such as benzene, toluene, xylene and the like.

It is preferred that the catalyst components be handled in an inert, moisture-free, oxygen free environment such as argon, nitrogen or helium because of the sensitivity of the catalyst components to moisture and oxygen.

In a preferred method, the Group IV B transition metal component and alumoxane are combined in a first step in a suitable solvent such as an aromatic solvent to produce a solution of the reaction product. This reaction may be carried out in the temperature range of −100° C. to about 300° C., preferably about 0° C. to about 100° C. Holding times to allow for the completion of the reaction may range from about 10 seconds to about 60 minutes depending on the reaction variables.

The solution produced by combining the Group IV B transition metal component and alumoxane is then contacted with the support. The method of contact may vary, but it is preferred that the support be added to the catalyst solution with vigorous stirring. Again contact temperatures may range from about 0° C. to about 100° C. depending upon the solvents used. Contact times may vary from about 10 seconds to about 60 minutes or longer.

The solvent can then be removed, typically by applying a vacuum. The solution may or may not be heated in order to aid in the removal of the solvent.

Regardless of the method used in the preparation, the active supported catalyst can be recovered by evaporation of the solvent to obtain a free-flowing solid or alternatively, the active supported catalyst can be maintained in its slurry state for direct use.

In accordance with this invention, optimum results are generally obtained wherein the alumoxane to Group IV B transition metal compound molar ratio is from about 1:1 to about 20,000:1, preferably for about 10:1 to about 1000:1. The Group IV B transition metal compound concentration on the support is typically between 0.01 wt % to about 100 wt %, preferably about 0.1 wt % to about 20 wt % based upon the weight of the support.

The Modified Supported Catalyst—Preparation Method

The modified supported catalyst of this invention can be prepared by combining in any order the Group IV B transition metal component, an alumoxane component, a modifier and the support in one or more suitable solvents or diluent. A modifier may be defined as a compound containing a Lewis acid or basic functionality, such as, for example, tetraethoxysilane, phenytriethyoxysilane bis-tert-butylhydroxytoluene (BHT), N,N-dimethylanaline and the like. Suitable solvents and/or diluents are the same as those described above.

It is preferred that the catalyst components be handled in an inert, moisture-free, oxygen free environment such as argon, nitrogen or helium because of the sensitivity of the catalyst components to moisture and oxygen.

In a preferred method, the alumoxane and the modifier are combined in a first step in a suitable solvent such as an aromatic solvent to produce a solution. The Group IV B transition metal compound is then added to this solution. These combined steps may be carried out in the temperature range of −100° C. to about 300° C., preferably about 0° C. Holding times to allow for the completion of the reaction may range from about 10 seconds to about 60 minutes depending on the reaction variables.

The solution produced by combining the Group IV B transition metal component, the alumoxane and the modifier is then contacted with the support. The method of contact may vary, but it is preferred that the support be added to the catalyst solution without vigorous stirring. Again contact temperatures may range from about 0° C. to about 100° C. depending upon the solvents used. Contact times may vary from about 10 seconds to about 60 minutes or longer.

The solvent can then be removed, typically by applying a vacuum. The solution may or may not be heated in order to aid in the removal of the solvent.

Regardless of the method used in preparation, the active supported catalyst can be recovered by evaporation of the solvent to obtain a free-flowing solid or alternatively, the active supported catalyst can be maintained in its slurry state for direct use.

In accordance with this invention, optimum results are generally obtained wherein the alumoxane to Group IV B transition metal compound molar ratio is from about 1:1 to about 20,000:1, preferably from about 10:1 to about 1000:1 and the alumoxane to modifier molar ratio is from about 1:1 to about 20,000:1, preferably from about 10:1 to about 1000:1. The Group IV B transition metal compound concentration on the support is typically between 0.01 wt % to about 100 wt %, preferably about 0.1 wt % to about 20 wt % based upon the weight of the support.

The Supported Catalyst—Preparation Method 3

In an alternative procedure the alumoxane component of the catalyst complex is prepared by direct reaction of a trialkyl aluminum or trialkyl aluminum mixtures with the material utilized as the catalyst support, such as an undehydrated silica gel. Silica useful as the catalyst support is that which has a surface area in the range of about 10 to about 700 m$^2$/g, preferably about 100–500 and desirably about 200–400 m$^2$, a pore volume of about 3 to about 0.5 cc/g and preferably 2-1 cc/g, and an adsorbed water content of from about 6 to about 20 weight percent, preferably from about 9 to about 15 weight percent. The average particle size (APS) of the silica may be from about 0.3μ to about 100μ, and for a gas phase catalyst preferably from about 30μ to about 60μ (1μ=10$^{-6}$ m). For a catalyst intended for high pressure polymerization the particle size of the silica should range from about 0.3 to no greater than about 10μ. Hereafter, silica having the above identified properties is referred to as undehydrated silica gel.

Undehydrated silica gel, as defined above, is added over time, about a few minutes, to a stirred solution of trialkyl aluminum, in an amount sufficient to provide a mole ratio of trialkyl aluminum to water of from about 3:1 to 1:2, preferably about 1.2:1 to 0.8:1. The trialkyl aluminum preferred for use in forming the alumoxane is trimethylaluminum. Next in order of preference, is triethylaluminum.

Upon addition of the undehydrated silica gel to the solution of trialkyl aluminum, the water content of the silica gel controllably reacts with the trialkyl aluminum to produce an alumoxane which is deposited onto the surface of the silica gel particles. Although the reaction of the trialkyl aluminum with the water content of the silica gel proceeds relatively quickly, that is, it is generally completed within the time of about 5 minutes, it does not occur with the explosive quickness of that which occurs with free water. The reaction may be safely conducted in conventional mixing equipment under a mantle of inert gas.

Thereafter a transition metal component is added to the stirred suspension of alumoxane silica gel product in an amount sufficient to provide a mole ratio of aluminum to transition metal of from about 1000:1 to about 1:1, preferably from about 300:1 to about 10:1 and most preferably from about 150:1 to about 30:1. The mixture is stirred for about 30 minutes to about one hour at ambient or an elevated temperature to permit the transition metal component to undergo complete reaction with the adsorbed alumoxane. Thereafter, the solvent is removed and the residual solids are dried, preferably at a temperature of 25° C. or greater, to a free flowing powder. The free flowing powder comprises a silica gel supported transition metal alumoxane catalyst complex of sufficiently high catalytic activity for use in the polymerization of olefins by conventional gas phase or liquid phase polymerization procedures.

The Prepolymerized Supported Catalyst

Upon completion of the deposition of the transition metal component, alumoxane and optionally a modifier on the support, the solid material can be treated with a small amount of monomer, e.g. ethylene, to form an amount of polymer on the solid catalyst materials to increase the catalyst weight at least 50%, desirably from about 100 to about 500% based on the total weight of catalyst and support material. Such treatment is hereafter referred to as prepolymerization of the catalyst. Then the solid material, as such or as prepolymerized, can be recovered by any well-known technique. For example, the solid catalyst material can be recovered from the liquid by filtration, by vacuum evaporation, or by decantation. The solid is thereafter dried under a stream of pure dry nitrogen or dried under vacuum.

Prepolymerization of the solid catalyst material aids in obtaining a polyolefin produced therefrom during slurry polymerization in well-defined particle form. The prepolymerized catalyst may be rinsed with a hydrocarbon to provide the good granular particle form. Prepolymerization also greatly reduces the requirement for alumoxane. For example, an Al:Transition Metal Component ratio of about 1000:1 or greater for alumoxane:Transition Metal Component is needed for high activity when the alumoxane is added to the liquid phase of the reactor, but a ratio less than 1000:1 is sufficient when the alumoxane is incorporated into the prepolymerized catalyst. For a prepolymerized catalyst the ratio of aluminum to transition metal may range from about 1:1 to 500:1, preferably from about 20:1 to 100:1, and high activities will still be obtained.

Most preferably, the prepolymerized supported catalyst is prepared in the following manner 1) forming a slurry by the addition of the alumoxane dissolved in a suitable solvent, toluene for example, to the support; 2) stirring the slurry at 60°-80° C. for 30-60 minutes; 3) removal of solvent under vacuum with heating sufficient to produce a dry powder; 4) adding a light hydrocarbon, pentane for example, to slurry the powder; 5) adding a solution of the transition metal component in pentane or a minimum amount of toluene and stirring for 15-60 minutes at 20°-60° C.; 6) prepolymerizing with ethylene or other olefin in the pentane slurry; and 7) then collecting, rinsing and drying the supported catalyst. For best particle form, it is preferred to add no alumoxane to the reactor beyond what is on the prepolymerized catalyst. Sufficient aluminum alkyl, such as triethylaluminum or triisobutylaluminum, to scavenge impurities in the feeds may be added, but not an excess.

Method of Use

The supported catalysts may be most usefully employed in gas or slurry phase processes, both of which are known to those of skill in the art. Thus, polymerizations using the invention supported catalysts may be conducted by either of these processes, generally at a temperature in the range of about 0°-160° C. or even higher, and under atmospheric, subatmospheric or superatmospheric pressure conditions.

A slurry polymerization process can utilize sub-or super-atmospheric pressures and temperatures in the range of −80°-250° C. In a slurry polymerization, a suspension of solid, particulate polymer is formed in a liquid polymerization medium to which ethylene, α-olefin, diolefin, cyclic olefin or acetylenically unsaturated comonomer, hydrogen and catalyst are added. Alkanes and cycloalkanes, such as butane, pentane, hexane, or cyclohexane, are preferred with $C_4$ to $C_{10}$ alkanes especially preferred. Preferred solvents also include liquid olefins which may act as monomers or comonomers including ethylene, propylene, butadiene, cyclopentene, 1-hexene, 3-methyl-1-pentene, 4-methyl-1-pentene, 1,4-hexadiene, 1-octene, 1-decene and the like.

A gas-phase polymerization process utilizes superatmospheric pressure and temperatures in the range of about 50° C. -120° C. Gas-phase polymerization can be performed in a stirred or fluidized bed of catalyst and product particles in a pressure vessel adapted to permit the separation of product particles from unreacted gases. Thermostated ethylene, comonomer, including α-olefins, diolefins, cyclic olefins or acetylenically unsaturated comonomer, hydrogen and an inert diluent gas such as nitrogen can be introduced or recirculated so as to maintain the particles at a temperature of 50°-120° C. Polymer product can be withdrawn continuously or semicontinuously at a rate such as to maintain a constant product inventory in the reactor. After polymerization and deactivation of the catalyst, the product polymer can be recovered by any suitable means. In commercial practice, the polymer product can be recovered directly from the gas phase reactor, freed of residual monomer with a nitrogen purge, and used without further deactivation or catalyst removal. The polymer obtained can be extruded into water and cut into pellets or other suitable comminuted shapes. Pigments, antioxidants and other additives, as is know in the art, may be added to the polymer.

While it is a characteristic of the invention supported catalyst that the produced polymers have a narrow molecular weight distribution, broad molecular weight distribution polymers may be produced by using two or more metallocenes or two or more activators.

EXAMPLES

In the examples which illustrate the practice of the invention the analytical techniques described below were employed for the analysis of the resulting polyolefin products. Molecular weight determinations for polyolefin products were made by Gel Permeation Chromatography (GPC) according to the following technique. Molecular weights and molecular weight distributions were measured using a Waters 150 gel permeation chromatograph equipped with a differential refractive index (DRI) detector and a Chromatix KMX-6 on-line light scattering photometer. The system was used at 135° C. with 1,2,4-trichlorobenzene as the mobile phase. Shodex (Showa Denko America, Inc.) polystyrene gel columns 802, 803, 804 and 805 were used. This technique is discussed in "Liquid Chromatography of Polymers and Related Materials III", J. Cazes editor, Marcel Dekker. 1981, p. 207, which is incorporated herein by reference. No corrections for column spreading were employed; however, data on generally accepted standards, e.g. National Bureau of Standards Polyethylene 1484 and anionically produced hydrogenated polyisoprenes (an alternating ethylene-propylene copolymer) demonstrated that such corrections on Mw/Mn (=MWD)

were less than 0.05 units. Mw/Mn was calculated from elution times. The numerical analyses were performed using the commercially available Beckman/CIS customized LALLS software in conjunction with the standard Gel Permeation package, run on a HP 1000 computer.

The following examples are intended to illustrate specific embodiments of the invention and are not intended to limit the scope of the invention.

All procedures were performed under an inert atmosphere of nitrogen. Solvent choices are often optional, for example, in most cases either pentane or 30–60 petroleum ether can be interchanged. The lithiated amides were prepared from the corresponding amines and either n-BuLi or MeLi. Published methods for preparing LiHC$_5$Me$_4$ include C. M. Fendrick et. al., *Organometallics*, 3:819 (1984) and F. H. Köhler and K. H. Doll, *Z. Naturforich*, 376:144 (1982). Other lithiated substituted cyclopentadienyl compounds are typically prepared from the corresponding cyclopentadienyl ligand and n-BuLi or MeLi, or by reaction of MeLi with the proper fulvene. TiCl$_4$ and ZrCl$_4$ were purchased from either Aldrich Chemical Company or Cerac. TiCl$_4$ was typically used in its etherate form. The etherate, TiCl$_4$.2Et$_2$O, can be prepared by gingerly adding TiCl$_4$ to diethylether. Amines, silanes, and lithium reagents were purchased from Aldrich Chemical Company or Petrarch Systems. Methylalumoxane (MAO) solutions were either toluene or heptane based and were supplied by either Schering or Ethyl Corp. The silica used was Davidson 948 grade, and was dried at 800° C. Triethylalumina (TEAL), supplied by Texas Alkyls as a 1.6M solution in heptane, was used as a scavenger in the polymerizations.

Preparation of Group IV B Transition Metal Components

Example A

Compound A

Part 1. Me$_4$HC$_5$Li (10.0 g, 0.078 mol) was slowly added to a Me$_2$SiCl$_2$ (11.5 ml, 0.095 mol, in 225 ml of tetrahydrofuran (THF) solution. The solution was stirred for 1 hour to assure complete reaction. The thf solvent was then removed via a vacuum to a cold trap held at −196° C. Pentane was added to precipitate the LiCl. The mixture was filtered through Celite. The solvent was removed from the filtrate. Me$_4$HC$_5$SiMe$_2$Cl (15.34 g, 0.071 mol) was recovered as a pale yellow liquid.

Part 2. Me$_4$HC$_5$SiMe$_2$Cl (10.0 g, 0.047 mol) was slowly added to a suspension of LiHN-t-Bu (3.68 g, 0.047 mol, ~100 ml THF). The mixture was stirred overnight. The thf was then removed via a vacuum to a cold trap held at −196° C. Petroleum ether (~100 ml) was added to precipitate the LiCl. The mixture was filtered through Celite. The solvent was removed from the filtrate. Me$_2$Si(Me$_4$HC$_5$) (HN-t-Bu) (11.4 g, 0.044 mol) was isolated as a pale yellow liquid.

Part 3. Me$_2$Si(Me$_4$HC$_5$) (HN-t-Bu) (11.14 g, 0.044 mol) was diluted with ~100 ml of Et$_2$O. MeLi (1.4M, 64 ml, 0.090 mol) was slowly added. The mixture was allowed to stir for 0.5 hours after the final addition of MeLi. The ether was reduced in volume prior to filtering off the product. The product, [Me$_2$Si(Me$_4$C$_5$) (N-t-Bu) ]Li$_2$ was washed with several small portions of ether, then vacuum dried.

Part 4. [Me$_2$Si(Me$_4$C$_5$) (N-t-Bu)]Li$_2$ (3.0 g, 0.011 mol) was suspended in ~150 ml of Et$_2$O. ZrCl$_4$ (2.65 g, 0.011 mol) was slowly added and the resulting mixture was allowed to stir overnight. The ether was removed via a vacuum to a cold trap held at −196° C. Pentane was added to precipitate the LiCl. The mixture was filtered through Celite twice. The pentane was significantly reduced in volume and the pale yellow solid was filtered off and washed with solvent. Me$_2$Si(Me$_4$C$_5$) (N-t-Bu) ZrCl$_2$ (1.07 g, 0.0026 mole) was recovered. Additional Me$_2$Si(Me$_4$C$_5$) (N-t-Bu) ZrCl$_2$ was recovered from the filtrate by repeating the recrystallization procedure. Total yield, 1.94 g, 0.0047 mol.

Example B

Compound B

Part 1. MePhSiCl$_2$ (14.9 g, 0.078 mol) was diluted with 250 ml of THF. Me$_4$HC$_5$Li (10.0 g, 0.078 mol) was slowly added as a solid. The reaction solution was allowed to stir overnight. The solvent was removed via a vacuum to a cold trap held at 196° C. Petroleum ether was added to precipitate the LiCl. The mixture was filtered through Celite and the pentane was removed from the filtrate. MePhSi(Me$_4$C$_5$H)Cl (20.8 g, 0.075 mol) was isolated as a yellow viscous liquid.

Part 2. LiHN-t-Bu (4.28 g, 0.054 mol) was dissolved in ~100 ml of THF. MePhSi(C$_5$Me$_4$H)Cl (15.0 g, 0.054 mol) was added dropwise. The yellow solution was allowed to stir overnight. The solvent was removed in vacuo. Petroleum ether was added to precipitate the LiCl. The mixture was filtered through Celite, and the filtrate was evaporated. MePhSi(C$_5$Me$_4$H) (NH-t-Bu) (16.6 g, 0.053 mol) was recovered as an extremely viscous liquid.

Part 3. MePhSi(C$_5$Me$_4$H) (NH-t-Bu) (17.2 g, 0.055 mol) was diluted with ~20 ml of ether. n-BuLi (60 ml in hexane, 0.096 mol, 1.6M) was slowly added and the reaction mixture was allowed to stir for ~3 hours. The solvent was removed in vacuo to yield 15.5 g (0.48 mol) of a pale tan solid formulated as Li$_2$[MePhSi(C$_5$Me$_4$) (N-t-Bu)].

Part 4. Li$_2$[MePhSi(C$_5$Me$_4$) (N-t-Bu)](8.75 g, 0.027 mol) was suspended in ~125 ml of cold ether (−30° C.). TiCl$_4$.2Et$_2$O(9.1 g, 0.027 mol) was slowly added. The reaction was allowed to stir for several hours prior to removing the ether via vacuum. A mixture of toluene and dichloromethane was then added to solubilize the product. The mixture was filtered through Celite to remove the LiCl. The solvent was largely removed via vacuum and petroleum ether was added. The mixture was cooled to maximize product precipitation. The crude product was filtered off and redissolved in toluene. The toluene insolubles were filtered off. The toluene was then reduced in volume and petroleum ether was added. The mixture was cooled to maximize precipitation prior to filtering off 3.34 g (7.76 mmol) of the yellow solid MePhSi(C$_5$Me$_4$) (N-t-Bu)TiCl$_2$.

Example C

Compound C

Part 1. (C$_5$Me$_4$H)SiMe$_2$Cl was prepared as described in Example A for the preparation of Compound A, Part 1.

Part 2. (C$_5$Me$_4$H)SiMe$_2$Cl (8.0 g, 0.037 mol) was slowly added to a suspension of LiHNC$_{12}$H$_{23}$ (C$_{12}$H$_{23}$=cyclododecyl, 7.0 g, 0.037 mol, ~80 ml THF). The mixture was stirred overnight. The THF was then removed via a vacuum to a cold trap held at −196° C. Petroleum ether and toluene were added to precipitate the LiCl. The mixture was filtered through Celite. The solvent was removed from the filtrate. Me$_2$Si(C$_5$Me$_4$H) (NHC$_{12}$H$_{23}$) (11.8 g, 0.033 mol) was isolated as a pale yellow liquid.

Part 3. Me$_2$Si(C$_5$Me$_4$H) (NHC$_{12}$H$_{23}$) (11.9 g, 0.033 mol) was diluted with ~150 ml of ether. MeLi (1.4M, 47 ml, 0.066 mol) was slowly added. The mixture was allowed to stir for 2 hours after the final addition of MeLi. The ether was reduced in volume prior to filtering off the product. The product, [Me$_2$Si(C$_5$Me$_4$)(NC$_{12}$H$_{23}$)]Li$_2$, was washed with several small portions of ether, then vacuum dried to yield 11.1 g (0.030 mol) of product.

Part 4. [Me$_2$Si(C$_5$Me$_4$) (NC$_{12}$H$_{23}$)]Li$_2$ (3.0 g, 0.008 mol) was suspended in cold ether. TiCl$_4$·2Et$_2$O (2.7 g, 0.008 mol) was slowly added and the resulting mixture was allowed to stir overnight. The ether was removed via a vacuum to a cold trap held at −196° C. Methylene chloride was added to precipitate the LiCl. The mixture was filtered through Celite. The solvent was significantly reduced in volume and petroleum ether was added to precipitate the product. This mixture was refrigerated prior to filtration in order to maximize precipitation. The solid collected was recrystallized from methylene chloride and Me$_2$Si(C$_5$Me$_4$)(NC$_{12}$H$_{23}$)TiCl$_2$ was isolated (1.0 g, 2.1 mmol).

Supported Catalyst Preparation and Use in Polymerization Procedures

Example 1

Dried silica (2.5 g) was slurried with 10 ml of 1.0M methylalumoxane (MAO) in toluene, and stirred for 0.5 hours. The slurry was then filtered and washed five times with 10 ml portions of pentane. The washed slurry was then dried under vacuum.

The transition metal compound, A, Me$_2$Si(Me$_4$C$_5$)(N-t-Bu)ZrCl$_2$ (0.063 g, 0.153 mmole) prepared as described for Example A, was combined with 35 ml of 1.0M MAO in toluene. The solution was stirred for five minutes prior to the addition of the treated silica (2.5 g). The mixture was then stirred for 5 minutes, after which time the toluene was removed via vacuum, and the prepared supported catalyst was recovered.

A polymerization run was performed in a 1 liter autoclave reactor equipped with a paddle stirrer, an external water jacket for temperature control, a regulated supply of dry nitrogen, ethylene, propylene, 1-butene and hexane, and a septum inlet for introduction of other solvents or comonomers, transition metal compound, and alumoxane solutions. The reactor was dried and degassed thoroughly prior to use.

A typical run consisted of injecting 400 ml of hexane, 0.2 ml TEAL (1.6M in heptane), and 0.5 g of the prepared supported catalyst into the reactor. The reactor was heated to 80° C. and 65 psi of ethylene was introduced prior to the injection of the prepared supported catalyst. The polymerization reaction was limited to 30 minutes. The reaction was stopped by rapidly cooling and venting the system. A mass of 20.2 g of polyethylene was recovered, having a molecular weight (MW) of 231,200, and a molecular weight distribution (MWD)=3.26.

Example 2

Dried silica (5.0 g) was slurried in 25 ml of toluene. MAO (12.5 ml, 1.0M) was added and the mixture was permitted to stir for five minutes. The transition metal compound A, Me$_2$Si(Me$_4$C$_5$) (N-t-Bu)ZrCl$_2$ (0.100 g, 0.243 mmole) prepared as described for Example A, was then added and the mixture was stirred for five minutes. Toluene was removed from the mixture via vacuum and the prepared supported catalyst was recovered.

Using the same general polymerization procedure as described for Example 1, 400 ml of hexane, 0.20 ml of triethylaluminum (TEAL) (1.6M in heptane), 0.50 g of the prepared supported catalyst, and 60 psi of ethylene were added to the reactor at 80° C. and allowed to react for 20 minutes. A mass of 1.9 g of polyethylene was recovered having a molecular weight of 170,900, and a MWD of 2.992.

Example 3

Dried silica was pretreated with methylalumoxane as described for Example 1. The transition metal compound B, MePhSi(Me$_4$C$_5$) (N-t-Bu)TiCl$_2$ (0.015 g, 0.035 mmol), prepared as described for Example B, was combined with 7.5 ml of 1.0M MAO in toluene and stirred for five minutes. Pretreated silica (0.5 g) was then added to this mixture with stirring for 5 minutes. The toluene was then removed via vacuum and the prepared supported catalyst was recovered.

Using the same general polymerization procedure as described for Example 1, 400 ml of hexane, 0.20 ml of TEAL (1.6M in heptane), 0.50 g of the prepared supported catalyst and 65 psi of ethylene were added to the reactor at 80° C. and allowed to react for 10 minutes. A mass of 10.7 g of polyethylene was recovered, having a molecular weight of 189,900, and a MWD of 3.652.

Example 4

The transition metal compound B, MePhSi(Me$_4$C$_5$)(N-t-Bu)TiCl$_2$ (0.015 g, 0.035 mmol), prepared as described for Example B, was combined with 5.0 ml of 1.5M MAO in heptane and stirred for five minutes. Dried silica, which had not been pretreated (0.5 g) was then added to this mixture with stirring for 5 minutes. The heptane was removed via vacuum and the prepared supported catalyst was recovered.

Using the same general polymerization procedure as described for Example 1, 400 ml of hexane, 0.20 ml of TEAL (1.6M in heptane), 0.50 g of the prepared supported catalyst and 65 psi of ethylene were added to the reactor at 80° C. and allowed to react for 15 minutes. A mass of 0.5 g of polyethylene was recovered having a molecular weight of 175,600 and a MWD of 2.801.

Example 5

The transition metal compound B, MePhSi(Me$_4$C$_5$)(N-t-Bu)TiCl$_2$ (0.015 g, 0.035 mmol), prepared as described for Example B, was combined with 7.5 ml of 1.0M MAO in toluene and stirred for five minutes. Dried silica (0.5 g), which had not been pretreated, was then added to this mixture with stirring for 5 minutes. The toluene was then removed via vacuum and the prepared supported catalyst was recovered.

Using the same general polymerization procedure as described for Example 1, 400 ml of hexane, 0.20 ml of TEAL (1.6M in heptane), 0.50 g of the prepared supported catalyst and 65 psi of ethylene were added to the reactor at 80° C. and allowed to react for 10 minutes. A mass of 3.1 g of polyethylene was recovered having a molecular weight of 313,900 and a MWD of 3.175.

Example 6

Dried silica (2.5 g) was slurried with 10 ml of 1.5M MAO in heptane and stirred for 0.5 hours. This slurry was then filtered, and washed five times with 10 ml portions of pentane, followed by drying in vacuo.

The transition metal compound B, MePhSi(Me$_4$C$_5$)(N-t-Bu)TiCl$_2$ (0.015 g, 0.035 mmol), prepared as described for Example B, was combined with 5.0 ml of 1.5M MAO in heptane and stirred for five minutes. Pretreated silica/(0.5 g) was then added to this mixture with stirring for 5 minutes. The heptane was removed via vacuum and the prepared supported catalyst was recovered.

Using the same general polymerization procedure as described for Example 1, 400 ml of hexane, 0.20 ml of TEAL (1.6M in heptane), 0.50 g of the prepared supported catalyst and 65 psi of ethylene were added to the reactor at 80° C. and allowed to react for 10 minutes. A mass of 2.0 g of polyethylene was recovered having a molecular weight of 365,900 and a MWD of 4.845.

Example 7

Dried silica (2.5 g) was slurried with 10 ml of 1.5M MAO in heptane and stirred for 0.5 hours. This slurry was then filtered, and washed five times with 10 ml portions of pentane. The washed slurry was dried under vacuum.

The transition metal compound C, Me$_2$Si(Me$_4$C$_5$)(NC$_{12}$H$_{23}$)TiCl$_2$ (40 mg, 0.084 mmol), prepared as described for Example C, was dissolved in 12.3 ml of 1.5M MAO in heptane and was permitted to stir 0.5 hours. Pretreated silica (2.5 g) was added, and the mixture stirred for an additional 0.5 hours. Toluene was then thoroughly removed via vacuum and the prepared supported catalyst was recovered.

The prepared supported catalyst (0.60 g), was placed in a 30 ml serum vial equipped with a magnetic stirring bar. While stirring, ethylene (5 psi) was allowed to flow into the vial forming a static pressure, and the reaction was permitted to proceed for 2.8 days. The vial was then vented and weighed. A mass of 5.5 g of polyethylene was recovered, having a molecular weight of 732,900 and an MWD of 2.980.

Example 8

A solution of 1.4M trimethylaluminum (TMA) in heptane (200 ml) was placed into a 1 L flask equipped with a magnetic stirring bar. Untreated silica gel (50 g), containing 9.6% water, was slowly added to the flask. After the addition of the silica was completed, the mixture was stirred at ambient temperature for one hour. The transition metal compound B, MePhSi(Me$_4$C$_5$)(N-t-Bu)TiCl$_2$ (1.35 g, 3.1 mmol), prepared as described for Example B, was slurried in 50 ml of heptane, and then added to the flask containing the treated silica. The mixture was permitted to react for one hour, and was then heated to 65° C. while a nitrogen stream was passed through the flask to remove the solvent. The nitrogen stream was stopped when the mixture in the flask turned into a free flowing powder.

A gas phase laboratory reactor was utilized with the following reactor conditions: 74° C., 300 psi, 50 mole % ethylene, 1 mole % hexene, 400 ppm hydrogen, cycle gas velocity 0.7 feet/sec, and TEAL feed rate (1% in isopentane) of 1 ml/hr. Polyethylene was recovered, (productivity 49 g/g) having the following properties: a molecular weight of 153,000, MWD of 4.817, 9 mole % hexene (as determined by $^1$H NMR), and density of 0.916.

Example 9

Dried silica (2.5 g) was slurried in 10 ml of 1.6M triethylaluminum (TEAL) in heptane and stirred for 0.50 hours. The slurry was then filtered and washed five times with 20 ml portions of pentane. The washed slurry was then dried under vacuum.

The transition metal compound, C, Me$_2$Si(Me$_4$C$_5$)N-C$_{12}$H$_{23}$TiCl$_2$ (0.010 g, 0.021 mmole) prepared as described for Example C, was dissolved in 5.0 ml of 1M MAO in toluene, which contained tetraethoxysilane (TEOS) (40 mg, 0.192 mmole) as a modifier, and was permitted to stir for 5 minutes. Pretreated silica (0.50 g) was added to this mixture with stirring for 5 additional minutes. Toluene was removed from the mixture via vacuum and the prepared supported catalyst was recovered.

Using the same general polymerization procedure described for Example 1, 400 ml of hexane, 0.50 g of the prepared supported catalyst and 65 psi of ethylene were added to the reactor at 80° C. and allowed to react for 0.50 hours. A mass of 13.2 g of polyethylene in fine particulate matter, was recovered, having a molecular weight of 221,055, and an MWD or 2.670.

Example 10

Dried silica (2.5 g) was slurried in 10 ml of 1.6M triethylaluminum (TEAL) in heptane and stirred for 0.50 hours. The slurry was then filtered and washed five times with 20 ml portions of pentane. The washed slurry was then dried under vacuum.

The transition metal compound, C, Me$_2$Si(Me$_4$C$_5$)N-C$_{12}$H$_{23}$TiCl$_2$ (0.010 g, 0.021 mmole) prepared as described for Example C, was dissolved in 5.0 ml of 1M MAO in toluene, and was permitted to stir for 5 minutes. Pretreated silica (0.50 g) was added to this mixture with stirring for 5 additional minutes. Toluene was removed from the mixture via vacuum and the prepared supported catalyst was recovered.

Using the same general polymerization procedure described for Example 1, 400 ml of hexane, 0.50 g of the prepared supported catalyst and 65 psi of ethylene were added to the reactor at 80° C. and allowed to react for 0.50 hours. A mass of 7.2 g of polyethylene in clusters of fine particles was recovered, having a molecular weight of 169,340, and a MWD of 4.999.

Table 2 summarizes the polymerization conditions employed and the properties obtained in the polymer products.

TABLE 2

Summary of Polyethylene Polymerization Results

| Example | Transition Metal (TM) Type | Transition Metal (TM) mmole | AT (MAO) mmole | Molar AL/TM Ratio | RXN Time (hr) | Yield (g) | Activity g/mmole TM. hr | MW | MWD |
|---|---|---|---|---|---|---|---|---|---|
| 1 | A | 0.031 | 7.0 | 230 | 0.50 | 20.2 | 1,300 | 231,200 | 3.26 |
| 2 | A | 0.024 | 1.25 | 50 | 0.33 | 1.9 | 240 | 170,900 | 2.99 |

TABLE 2-continued

Summary of Polyethylene Polymerization Results

| Example | Transition Metal (TM) Type | Transition Metal (TM) mmole | AT (MAO) mmole | Molar AL/TM Ratio | RXN Time (hr) | Yield (g) | Activity g/mmole TM. hr | MW | MWD |
|---|---|---|---|---|---|---|---|---|---|
| 3 | B | 0.035 | 7.5 | 210 | 0.17 | 10.7 | 1,800 | 189,900 | 3.65 |
| 4 | B | 0.035 | 7.5 | 210 | 0.25 | 0.5 | 60 | 175,600 | 2.80 |
| 5 | B | 0.035 | 7.5 | 210 | 0.17 | 3.1 | 520 | 313,900 | 3.18 |
| 6 | B | 0.035 | 7.5 | 210 | 0.17 | 2.0 | 340 | 365,900 | 4.85 |
| 7[a] | C | 0.020 | 4.4 | 220 | 66.5 | 5.5 | 4 | 732,900 | 2.98 |
| 9[b] | B | 0.021 | 5.0 | 240 | 0.50 | 13.2 | 1,260 | 221,100 | 2.67 |
| 10 | B | 0.021 | 5.0 | 240 | 0.50 | 7.2 | 690 | 169,300 | 5.00 |

[a]Gas Phase Polymerization
[b]TEOS Modifier Used

By appropriate selection of (1) Group IV B transition metal component for use in the catalyst system; (2) the type and amount of alumoxane used whether preformed or generated in situ; (3) the choice of support material; (4) the method of support; (5) the choice of a modifier if used; (6) the polymerization diluent type and amount if used; (7) the reaction temperature; (8) the reaction pressure and (9) the process used whether it be slurry, bulk or gas phase, polymers of a desired combination of properties are produced.

The invention has been described with reference to its preferred embodiments. Those of ordinary skill in the art may, upon reading this disclosure, appreciate changes or modifications which do not depart from the scope and spirit of the invention as described above or claimed hereafter.

We claim:

1. A process for the polymerization of one or more olefins comprising contacting the monomer or monomers under polymerization conditions in the presence of a catalyst system comprising:
   (A) an inert support;
   (B) a transition metal compound represented by the formulae:

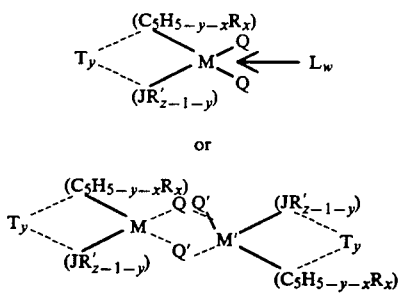

wherein
M is Zr, Hf, or Ti in its highest formal oxidation state:

$(C_5-H_{5-y-x}R_x)$ is a cyclopentadienyl ring which is substituted with from zero to five substituent groups R, "x" is 0, 1, 2, 3, 4 or 5 denoting the degree of substitution, and each substituent group R is, independently, a radical selected from a group consisting of $C_1-C_{20}$ hydrocarbyl radicals; substituted $C_1-C_{20}$ hydrocarbyl radicals wherein one or more hydrogen atoms is replaced by a halogen radical, an amido radical, a phosphido radical, an alkoxy radical, an alkylborido radical, or other radical containing a Lewis acidic or basic functionality; $C_1-C_{20}$ hydrocarbyl-substituted metalloid radicals wherein the metalloid is selected from the Group IV A of the Periodic Table of Elements; and halogen radicals, amido radicals, phosphido radicals, alkoxy radicals, alkylborido radicals, or a radical containing Lewis acidic or basic functionality; or $(C_5H_{5-y-x}R_x)$ is a cyclopentadienyl ring in which two adjacent R-groups are joined forming $C_4-C_{20}$ ring to give a saturated or unsaturated polycyclic cyclopentadienyl ligand;

$(JR'_{z-1-y})$ is a heteroatom ligand in which J is an element with a coordination number of three from Group V A or an element with a coordination number of two from Group VI A of the Periodic Table of Elements, each R' is, independently a radical selected from a group consisting of $C_1-C_{20}$ hydrocarbyl radicals; substituted $C_1-C_{20}$ hydrocarbyl radicals wherein one or more hydrogen atom is replaced by a halogen radical, an amido radical, a phosphido radical, an alkoxy radical, an alkylborido radical, or other radical containing a Lewis acidic or basic functionality; and "z" is the coordination number of the element J;

each Q is, independently, any univalent anionic ligand provided that where Q is a hydrocarbyl ligand such Q cannot be a substituted or unsubstituted cyclopentadienyl ring or both Q together are an alkylidene, a cyclometallated hydrocarbyl or a divalent anionic chelating ligand;

"y" is 0 or 1 when "w" is greater than 0; "y" is 1 when "w" is 0; when "y" is 1, T is a covalent bridging group containing a Group IV A or V A element;

L is a neutral Lewis base where "w" denotes a number from 0 to 3; and (C) an alumoxane.

2. The process of claim 1 wherein the heteroatom ligand group J element is nitrogen, phosphorous, oxygen or sulfur.

3. The process of claim 1 wherein Q is a halogen or hydrocarbyl radical.

4. The process of claim 2, wherein the heteroatom ligand group J element is nitrogen.

5. The process of claim 1 wherein M is titanium or zirconium.

6. The process of claim 1 wherein the aluminum atom to transition metal atom mole ratio is from about 10:1 to about 1,000:1.

7. The process of claim 1 wherein the support is an inorganic support selected from the group consisting of talc, silica, alumina, silica-alumina, magnesia, titania, zirconia, or mixtures thereof.

8. The process of claim 7, wherein said support is dehydrated.

9. The process of claim 1, further comprising a modifier compound containing a Lewis acidic or basic functionality.

10. The process of claim 1, wherein the aluminum atom to transition metal atom mole ratio is about 10:1 to about 20,000:1.

11. The process of claim 1, wherein the alumoxane is formed on the support by reaction of a hydrated support with a trialkylaluminum.

12. The process of claim 7, wherein the hydrated support is silica containing from about 6 to about 20 weight percent water and is reacted with trimethylaluminum.

* * * * *